United States Patent [19]
Lowell et al.

[11] Patent Number: 6,021,661
[45] Date of Patent: Feb. 8, 2000

[54] APPARATUS FOR DETERMINING PORE VOLUME DISTRIBUTION OF MULTIPLE SAMPLES BY INTRUSION OF A NON-WETTING LIQUID

[75] Inventors: Seymour Lowell; Stuart S. Warszycki, both of Lake Worth; David W. Sumell, Loxahatchee, all of Fla.

[73] Assignee: Quantachrome Corporation, Boynton Beach, Fla.

[21] Appl. No.: 09/080,476

[22] Filed: May 18, 1998

[51] Int. Cl.⁷ .................................................. G01N 15/08
[52] U.S. Cl. ............................................................. 73/38
[58] Field of Search ....................................... 73/38

[56] References Cited

U.S. PATENT DOCUMENTS

| | | | |
|---|---|---|---|
| 3,371,520 | 3/1968 | Slone et al. | 73/38 |
| 4,170,129 | 10/1979 | Lowell | 73/38 |
| 4,272,983 | 6/1981 | Sisti et al. | 73/38 |
| 4,644,779 | 2/1987 | Sisti et al. | 73/38 |
| 5,569,839 | 10/1996 | Ajot et al. | 73/38 |

*Primary Examiner*—Daniel S. Larkin
*Attorney, Agent, or Firm*—Malin, Haley & DiMaggio, P.A.

[57] ABSTRACT

A high pressure mercury porosimeter for continuous pore volume distribution measurements that simultaneously receives two or more test sample penetrometers, each containing a powder or porous solid sample to be tested. Two or more individual tests can be simultaneously performed per high pressure cycle in a single porosimeter. Only one access port is required to access 2 or more penetrometers greatly increasing sampling throughput, reducing multiple test time requirements without significant equipment cost increase.

13 Claims, 4 Drawing Sheets

APPARATUS FOR DETERMINING PORE VOLUME DISTRIBUTION OF MULTIPLE SAMPLES BY INTRUSION OF A NON-WETTING LIQUID

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to apparatus for determining the pore volume distribution of a powdered or porous solid sample by non-wetting liquid intrusion, and more particularly to a mercury porosimeter that provides for determining the pore volume distribution of two or more samples simultaneously by intrusion and extrusion of a non-wetting liquid such as mercury under ascending and descending pressures between ambient to 60,000 psi for pore size analysis from approximately 5 microns to 0.0036 microns.

2. Description of Related Art

Many materials, both natural and man-made, contain pores that range in depth and diameter from a few Angstroms to a few millimeters. Measuring the smallest pores, called micropores, is done most accurately by gas sorption. Mesopores, which are intermediate size pores, are commonly measured by either gas sorption or high-pressure mercury intrusion. Larger pores, called macropores, and the voids between closely packed or compressed particles, are best suited for a method of low-pressure mercury intrusion.

This invention relates to the measurement of mesopores and small macropores with the use of high-pressure mercury intrusion.

Mercury porosimeters operate upon a physical principle that a non-reactive, non-wetting liquid will not penetrate fine pores until sufficient pressure is applied to force its entry. The relationship between the applied pressure and the pore diameter into which mercury will intrude is given by the Washburn equation:

$$P = (-4 \gamma \cos \theta) \div D$$

where P is the applied pressure, D is the pore diameter, $\gamma$ is the surface tension of mercury, 480 dynes per $CM^{-1}$, and $\Theta$ is the contact angle between mercury and the pore wall, usually taken as 140°. The mercury porosimeter monitors the volume of mercury intruded into and extruded from the sample as a function of pressure, which permits analytically generating pore size and volume distributions from the Washburn equation. When dealing with mesopores and macropores, high-pressure mercury intrusion and extrusion is utilized. A porosimeter must be able to subject mercury to pressures ranging between ambient to 60,000 psi which allows for pore size analysis from around 5 microns to 0.0036 microns pore diameter.

U.S. Pat. No. 4,170,129 (the '129 patent) discloses a method for determining the pore volume distribution of a powder sample by mercury intrusion, and measurement over a continuously ascending pressure. The '129 patent establishes the heretofore preferred method of determining the pore volume distribution of a powder sample by mercury intrusion.

As discussed in the '129 patent, the pore volume distribution of a powder or porous solid sample is desired for manufacturing of various materials such as filters, adsorbents, catalysts, porous rock separators, and the like. In certain of these materials such as used for metal and ceramic parts, structural failure can be anticipated if they have excessive pores. Alternately, materials used for catalysts should have open and accessible pores.

A conventional mercury porosimeter is comprised of a rigid housing having a high pressure cavity that can withstand internal pressures of sixty thousand pounds per square inch (psi). A penetrometer containing a test sample is mounted in the high pressure cavity. The penetrometer, including its capillary, is filled with mercury. A portion of the housing high pressure cavity that contains the penetrometer capillary includes typically a metal sheath that functions as one plate of an electrical capacitor. The penetrometer also includes an electrode that is in contact with the mercury contained within the capillary which also functions as the other plate of an electrical capacitor. As pressure is applied, the column of mercury recedes in the capillary changing the capacitance between the two plates. A mathematical relationship between the electrical capacitance measured and the volume of mercury is clearly established which is used in conjunction with internal pressure to obtain the proper mercury intrusion and extrusions curves for measuring pore volume distribution.

Finally, a plot of the measured data shows the relationship between the mercury intruded, the applied pressure, and the pore diameter.

In applications utilizing the hereinabove described techniques for determining pore size, multiple sample measurements are often desired for various reasons. To verify measurements and accuracies, dual test samples are often taken and run back to back. However, running back to back samples essentially doubles the time requirement for each test sequence. Each test requires placing a single test penetrometer containing the sample and a quantity of mercury into the apparatus. The sample in the apparatus must then be pressurized from ambient up to approximately 60,000 psi and back to ambient while making and recording sensitive capacitive measurements.

In a conventional high-pressure mercury porosimeter, because of the extremely high pressures involved, access to the high-pressure cavity is done through a single threaded port that accesses essentially a single cavity that tests individual samples. Each time the high-pressure porosimeter is used, a single sample is taken and the machine must be sealed and closed tightly, ascending and descending pressures applied while the sample readings are taken, and then the pressure withdrawn to remove the sample. Taking a series of individual test samples in serial relationship is, thus, a time consuming process, especially if the user has a large volume of different samples that must be analyzed.

The present invention overcomes the problems of the prior art by providing a high-pressure mercury porosimeter that has a single access port that contains a cavity that includes two or more penetrometers, each having a capillary so that two independent samples can be tested under high pressure, up to 60,000 psi, that requires substantially the same amount of time between start-up and shut-down as previously experienced using a single sample. This greatly increases the efficiency of the porosimeter and greatly reduces the per sample analysis time. The present invention accomplishes this without greatly increasing the internal volume of the porosimeter, which would adversely affect the ability to attain the high pressures involved (60,000 psi). The larger the volume of the cavity, the more oil is needed to create the high pressures required resulting in greater compressibility factors which can physically limit present day equipment from obtaining 60,000 psi. Using the present invention, two or more independent separate powder or porous solid samples can be obtained simultaneously, up to 60,000 psi, for pore size analysis of samples ranging from 5 microns to 0.0036 microns, by requiring only a single port access to the high-pressure housing and cavity.

BRIEF SUMMARY OF THE INVENTION

A high-pressure mercury porosimeter for performing two or more independent, separate sample tests simultaneously in a pressure vessel having a single sample access port. The apparatus provides continuous or step-wise pore volume distribution measurements comprising a housing having internal high-pressure chambers, capable of withstanding internal pressures of 60,000 psi that simultaneously receives two or more test sample penetrometers, each containing a powder or porous solid sample to be tested and a quantity of non-wetting liquid such as mercury. The mercury is disposed in intruding relation to each sample, and the samples are simultaneously placed under continuously or step-wise ascending and descending pressures to intrude and extrude the mercury into and out of the pores of the samples through a capillary access to each penetrometer.

During the ascending and descending pressurization process, the pressure and volume intruded and extruded into and out of the samples is measured and recorded. Preferably, an incompressible fluid such as hydraulic oil is placed in an interposed position between the mercury and a pressurizing piston to develop the pressure needed to intrude the mercury into the pores of the powder or porous solid samples. Descending pressure allows for some extrusion of the intruded mercury from the pores.

The porosimeter housing includes two or more internal high-pressure chambers that are strategically sized in volume and shape to each receive its own penetrometer which contains each test sample. Each penetrometer also has at its base an individual electrode that is in electrical communication with the mercury inside the penetrometer.

The porosimeter housing and, in particular, the internal high pressure chambers are accessible through a single sample insertion and retrieval access port from the top that receives a cylindrical cap that has two or more capillary chambers that are strategically sized longitudinally to receive each capillary that is attached to each penetrometer that contain the samples. A threaded, locking nut includes an axial passage that firmly locks the cylindrical cap and attaches the cap sealably to the housing. The cylindrical cap and penetrometer chambers are capable of sustaining pressures up to 60,000 psi. Each capillary chamber terminates in ports that are in fluid communication with one or more solenoid-activated valves that control air venting to purge air from the system at start up.

The porosimeter housing also includes a bottom passage that is threaded that receives a bottom end cap that contains two or more electrodes, one for each penetrometer that is utilized to obtain capacitance readings used for the intrusion and extrusion measurements to obtain pore volume. The housing and the top cylindrical cap and the bottom end cap include sufficient O-rings and seals to insure the pressure integrity when the porosimeter is in use and under high pressure.

The volume of the housing internal high pressure chambers that receive the penetrometers and the additional volume for the capillary chambers are strategically sized and shaped to obtain operational pressures up to 60,000 psi with hydraulic oil.

The housing also includes an inlet oil passage that communicates from outside the housing to the internal high pressure chambers and capillary chambers for applying high-pressure incompressible hydraulic oil. The penetrometer and capillaries used for each sample are conventional in construction and can be varied in size and shape, depending on the particular samples to be taken.

Each sample electrode, one for each penetrometer, is individually connected electrically from each penetrometer to a capacitance measuring device and then to a computer, where the resultant signals can be analyzed simultaneously through multiplexing techniques to get the proper volume measurements at various pressure ranges. Hydraulic oil pressure is obtained from a piston and a high-pressure oil chamber that can be longitudinally displaced through a continuous threaded rod driven by an AC motor.

The system also includes a conventional oil pump and vent valves sealably connected to and in fluid connection with the capillary chambers that allow air to be purged from the system prior to the system being charged to a high pressure to purge unwanted air.

Obtaining the mercury intrusion and extrusion values for two or more porous samples can be done simultaneously with one ambient-high-ambient pressure cycle to the porosimeter, depending on the number of penetrometers disposed within the housing. Each capillary chamber wall formed by cylindrical wall within the end cap is an electrical conductor and comprises one plate of each capacitor formed between the mercury inside each capillary and penetrometer, the conductive top cap being grounded as is the capacitance measuring device.

Thus, it can be seen using the present invention, two or more samples can be treated through a single access to the housing, requiring a single placement of the capillary end cap and the hydraulic pressure of one intrusion/extrusion cycle requiring approximately the same amount of time as in conventional high-pressure mercury porosimeters that use a single sample. Therefore, sample throughput analyses can be effectively doubled or tripled using the present invention without greatly increasing the cost or the complexity of the porosimeter structure itself.

Although the present invention has been described using capacitance based on the electrical conductivity of mercury to measure volume of intrusion and extrusion of the mercury, other known methods can be used which include measuring the electrical resistance of the mercury instead of the capacitance. Thus, the invention could be utilized with other system elements that can measure the mercury volume in the capillary other than electrical capacitance.

Accordingly, it is an object of the present invention to provide a high-pressure mercury porosimeter having multiple sample receiver penetrometer chambers for simultaneously determining the pore volume distribution of two or more discrete samples by mercury intrusion.

It is another object of the present invention to provide a multi-chamber apparatus for simultaneously determining the pore volume distribution of two or more discrete powder or porous solid samples by high pressurization of a non-wetting liquid, such as mercury, and continuously measuring the pressure and volume of the non-wetting liquid intruded into the samples.

In accordance with these and other objects which will become apparent hereinafter, the instant invention will now be described with particular reference to the accompanying drawings.

DETAILED DESCRIPTION OF THE INVENTION

Figure 1:
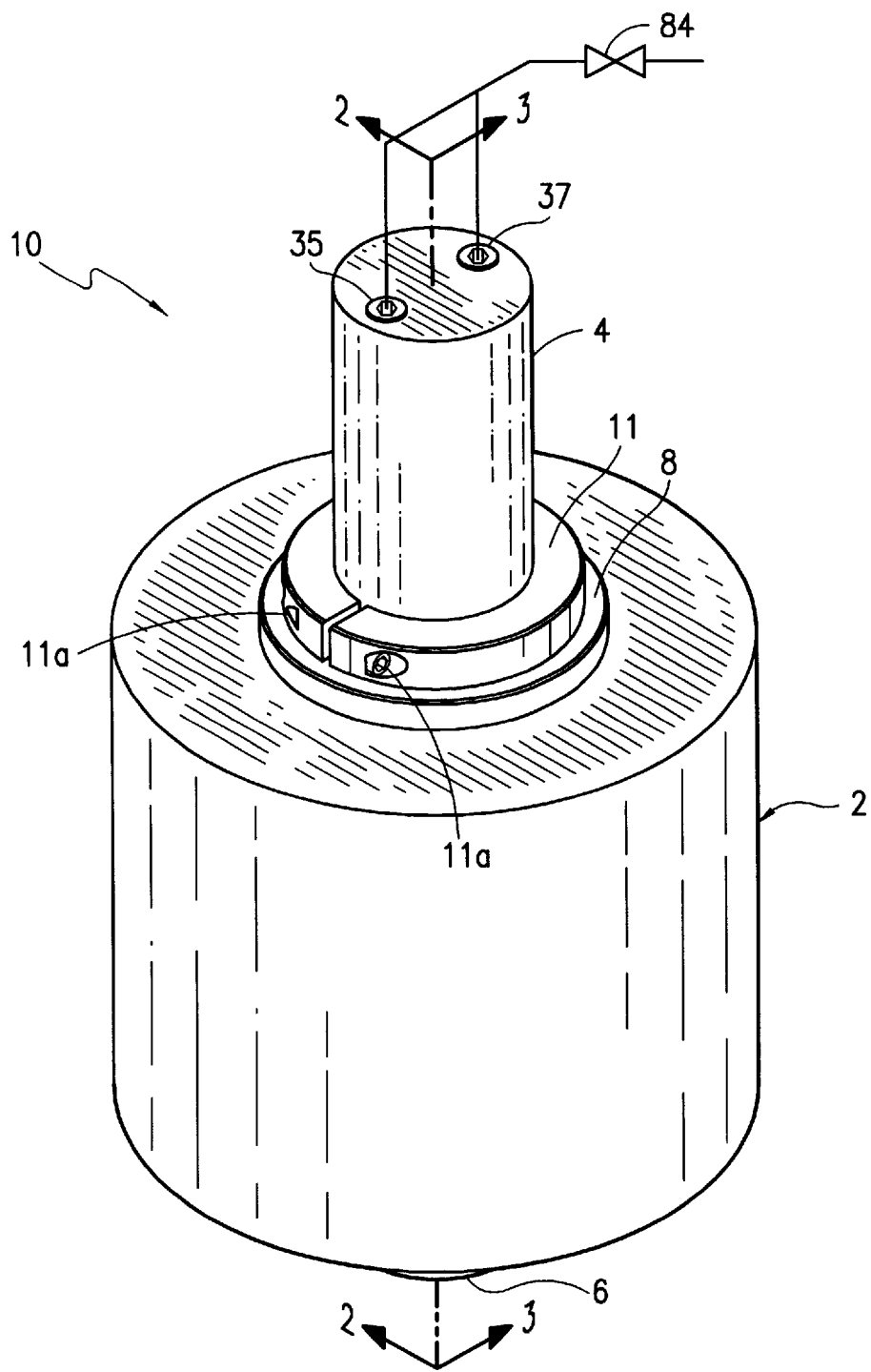
FIG. 1 is a perspective view of one embodiment of the present invention.

Referring to FIG. 1, one embodiment of the present invention is illustrated generally comprising high-pressure, cylindrical, rigid housing 2, a removable sample access cap 4, and bottom end cap 6, which in combination comprise a high-pressure mercury porosimeter 10. Access cap 4 is threadably attached (removably) and held within housing 2 by threaded nut 8, and a locking collar 11. Housing 2, housing access cap 4, and bottom end cap 6 are made of a suitable material, such as metal including stainless steel, which can provide, in combination, a pressure vessel that is capable of safe internal pressurization of up to approximately 60,000 psi. Access cap 4 is made of an electrically conductive material.

Figure 2:
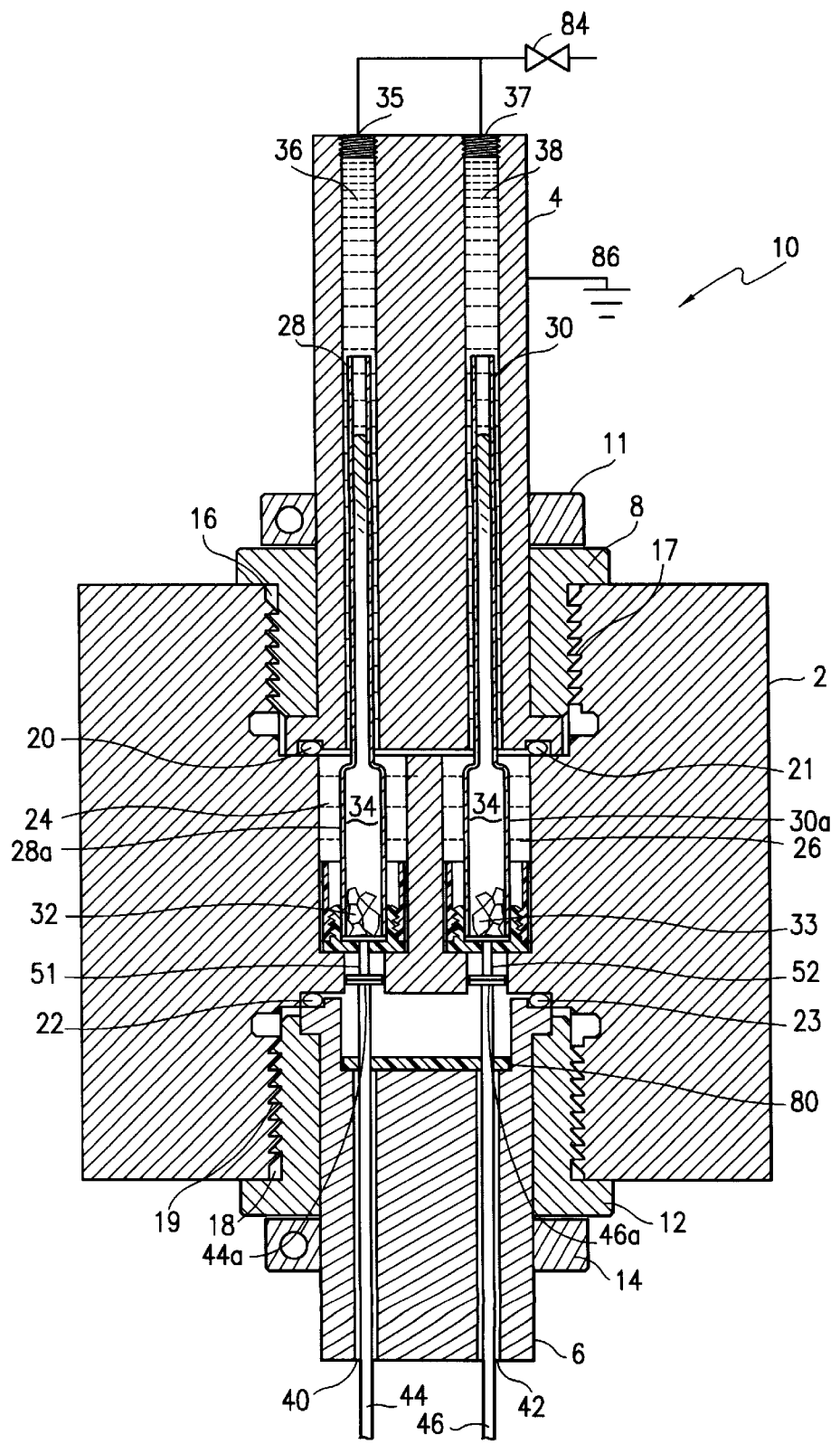
FIG. 2 is cross-sectional view taken along line 2—2 in FIG. 1.

Referring to FIG. 1 and FIG. 2, bottom end cap 6 is connected to housing 2 by threaded nut 12, and locking collar 14. Housing 2 includes a top internally threaded access port 16, and bottom internally threaded port 18. Access cap 4 is placed within port 16 and nut 8 is threaded into mating internal threads 17 causing a suitable seal with O-ring 20 to seal against adjacent machined O-ring surfaces 21 each time samples within penetrometers are loaded and unloaded. Locking collar 11, which can be a conventional split ring device, joined together with fasteners 11a, may be utilized to retain nut 8 in place by preventing nut 8 from slipping off the distal end of access cap 4 when not installed within housing 2. Removal of access cap 4 and nut 8 provides access to the test samples through single port 16. Access cap 4 also has two or more high pressure capillary chambers 36 and 38 each of which receives a capillary 28 and 30 adjoined to each penetrometer 28a and 30a.

Bottom end cap 6 is mounted within port 18 and nut 12 is threaded into mating internal threads 19 causing O-ring 22 to seal against adjacent machined O-ring surfaces 23. Locking collar 14, which can be a conventional split ring device, is utilized to retain nut 12 in place by preventing nut 12 from slipping off the distal end of bottom end cap 6 when not installed within housing 2.

Figure 3:
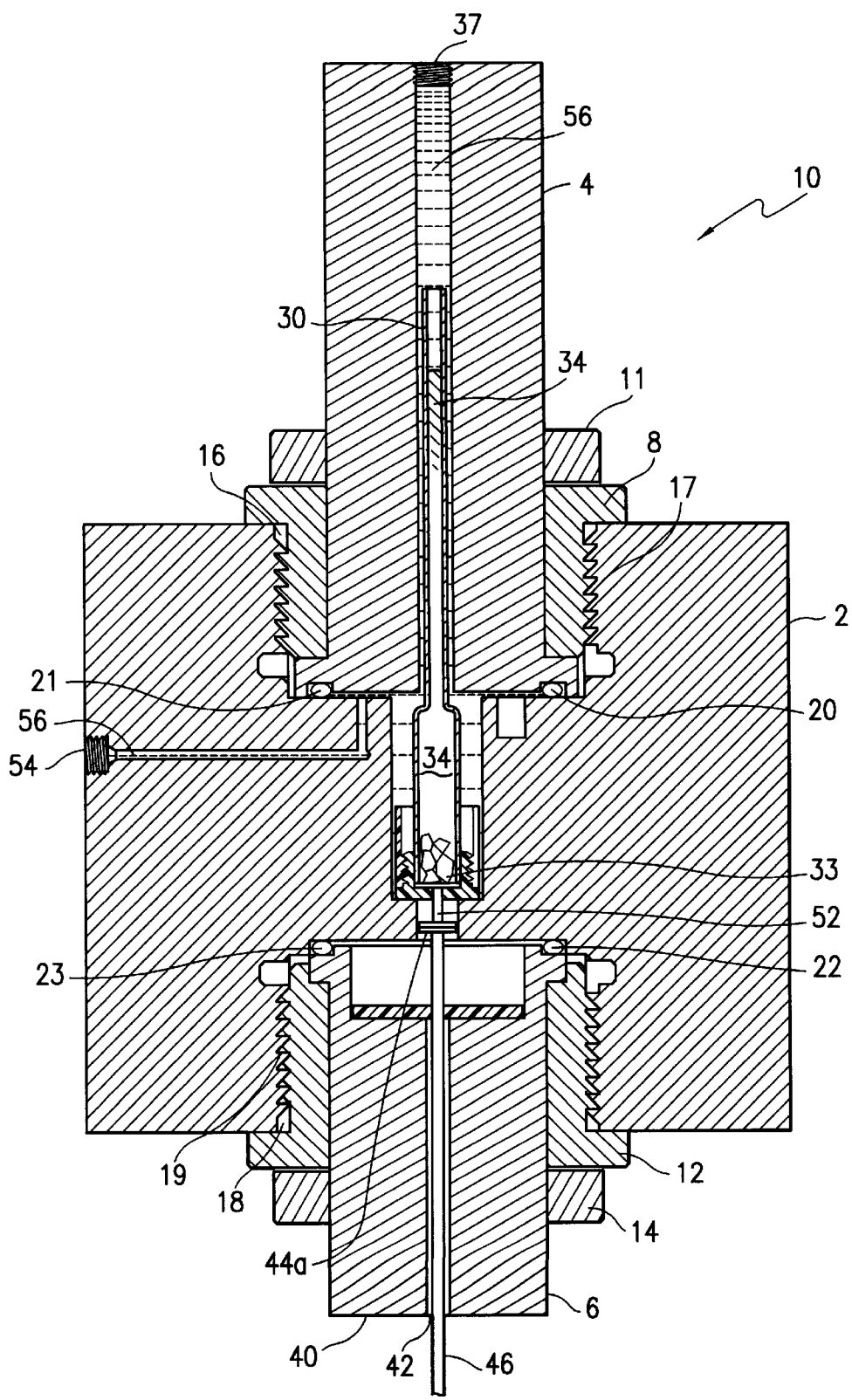
FIG. 3 is cross-sectional view taken along line 3—3 in FIG. 1.

Referring to FIGS. 2 and 3, housing 2 further includes internal high pressure sample chambers 24 and 26 sized to simultaneously receive penetrometers 28a and 30a, respectively. Penetrometers 28a and 30a, are conventional devices, typically made of glass, containing powder or porous solid samples 32 and 33, and a quantity of a non-wetting liquid such as mercury 34. Access cap 4 includes capillary passages 36 and 38 to simultaneously receive the capillaries 28 and 30. Capillary passages 36 and 38 are in fluid communication with solenoid activated valves 84 that vent air from the capillary chambers through end connectors 35 and 37.

Bottom end cap 6 includes an electrical insulator 80 and apertures 40 and 42 that contain electrical probe connectors 44 and 46 in electrical contact with electrodes 51 and 52 of penetrometers 28a and 30a, respectively. The electrodes 51 and 52 are in electrical contact with the mercury 34. An electrical capacitor is formed between the mercury 34 in each separate sample capillary which is electrically connected to a capacitance measurement device described below and the inside walls of chambers 36 and 38 of conductive top cap 4 which are connected to electrical ground 86.

Inlet port 54 (FIG. 3) provides an access for the input under pressure of an incompressible fluid, such as hydraulic oil 56. In FIG. 2 during a test cycle from ambient to high pressure, hydraulic oil 56 is forced under ascending pressure into housing 2 forcing mercury 34, contained within capillaries 28 and 30, into samples 32 and 33 in penetrometers 28a and 30a. As the hydraulic oil 56 is forced continuously or in step-wise fashion into housing 2, capacitive measurements are simultaneously recorded separately for each sample and the increasing hydraulic pressure is measured and recorded. Internal air is vented through end connectors 35 and 37 when filling with hydraulic oil 56 in preparation for pressurization of the ascending pressure to approximately 60,000 psi. As the oil pressure is reduced during descending pressure, extrusion values can be obtained.

Using the porosimeter shown in FIGS. 1, 2, and 3, capacitive measurements are utilized to determine the amount of mercury intruded and extruded into and out of the samples 32 and 33. As the amount of mercury intruded relative to the applied ascending pressure is determined, the pore volume distribution can be determined for each sample 32 and 33. During descending pressure, extrusion values are obtained back to ambient pressure.

Figure 4:
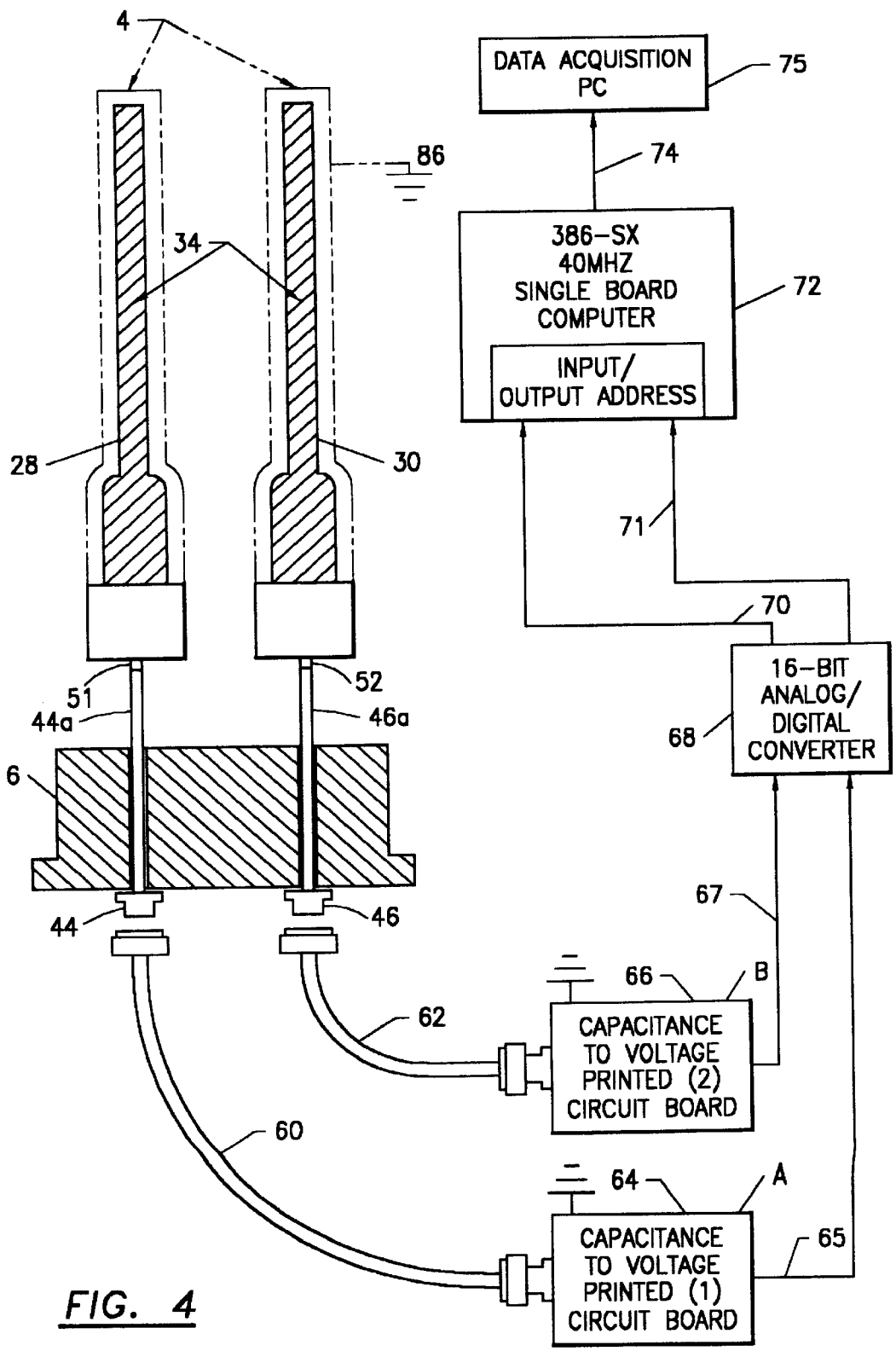
FIG. 4 is a diagrammatic illustration of the data collection system and method of the present invention.

Referring to FIG. 2 and FIG. 4, one embodiment for the data collection system and method for the present invention is illustrated. Capillaries 28 and 30 containing mercury are positioned within capillary passages 36 and 38. Access cap 4 provides electrically grounded (ground 86) stainless steel conductive capillary passages 36 and 38, the walls of which act as capacitor plates around both capillaries 28 and 30, forming individual plates of two separate capacitors. Mercury 34 contained within capillaries 28 and 30 and penetrometers 28a and 30a comprise separate plates of capacitance, and juxtaposed with the plates (walls) of capillary passages 36 and 38 in access cap 4, two different capacitors are formed, capacitor A and capacitor B, associated with capillaries 28 and 30, respectively.

As mercury is intruded under ascending pressure into the test samples, the level of mercury drops within each capillary 28 and 30. The change in mercury level changes the capacitive readings of each capacitor. The change of mercury level, and resultant capacitance change, indicates the amount of mercury intruded into each test sample and the pore volume.

Electrical connection to the mercury in capillaries 28 and 30 and penetrometers 28a and 30a is provided by electrodes 51 and 52, contacts 44a and 46a, and wires 44 and 46, leading to the outside of bottom cap 6. Interconnect cables 60 and 62, which can be RG 58 C/V cable with BNC connectors, connect the test sample capillaries 28 and 30 to capacitance to voltage converters 64 and 66, respectively, which are electrically grounded. Analog voltage 65 and 67 from capacitance to voltage converters 64 and 66, respectively, are connected to an analog to digital (A/D) converter 68, which in this embodiment can be a 16-bit converter.

The digital output 70 and 71 from A/D converter 68 is connected to a single board computer 72, which in this embodiment can be included a 386-SX microprocessor running at 40 MHz. The computer 72 sends the digital data streams 70 and 71 to a data acquisition computer 75 via an RS-232 serial interface 74. Data acquisition computer 75 can be any suitable personal or portable computer.

The continuously or step-wise increasing and decreasing pressures within porosimeter 10 are also measured and input to data acquisition computer 75 (not shown). Data acquisition computer 75 includes programmable software to provide conversion of the raw pressure and capacitance data to the desired pore volume distribution of each test sample.

The invention 10 provides for simultaneous testing of two or more samples during one pressurization cycle. Only one port access opening is required (removal of access cap 4) to process two or more samples per test cycle. The embodiment hereinabove described is believed to be the best mode of the invention. The configuration of housing 2, access cap 4, and bottom end cap 6 is believed to be the most convenient configuration, as-well-as providing, in combination, a pressure vessel 10 that utilizes a minimum amount of raw material in construction and results in a compact structure. The internal capillary and penetrometer chamber volume of 70 cc is selected to ensure that pressures up to 60,000 psi can be obtained.

However, other embodiments can be configured utilizing the invention. For example, housing 2, and/or top cap 4 and/or end cap 6 can be made in a shape other than cylindrical to practice the invention. While other configurations are possible, the embodiment described hereinabove is more convenient, less costly to manufacture, and is the preferred embodiment.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A high pressure mercury porosimeter for determining the pore volume distribution of two or more samples by intruding and extruding a non-wetting electrically conductive liquid into each of the samples under continuously or step-wise ascending pressure above ambient psi, comprising:

a housing having an internal, cavity, said housing cavity including a pair of chambers, each chamber strategically sized in volume and configuration shape to receive at least one penetrometer, each penetrometer having a capillary attached thereto capable of receiving a preselected amount of a non-wetting liquid; said housing including one loading access port to said internal cavity;

a top cap removably and sealably connectable to said access port of said housing, said top cap having at least two elongated electrically conductive passages, each passage sized to receive one of said capillaries attached to one of said penetrometers;

electrical circuit means between said conductive non-wetting liquid in said penetrometers to a location outside of said housing; and means for electrically grounding said top cap conductive chambers;

said housing and said top cap together defining a pressure vessel for ascending and descending pressurization of each of said samples intruding and extruding said non-wetting liquid into and out of said samples, including means for simultaneous measurement of said ascending and descending pressure and electrical capacitance between said top cap passage walls and said conductive non-wetting liquid in said penetrometers.

2. The porosimeter of claim 1 including a bottom end cap, said housing having a bottom end cap access port for sealably receiving said bottom end cap, said bottom end cap having passages for said circuit means.

3. The porosimeter of claim 2 further including a pressurization port in fluid communication with said pressure vessel and an incompressible liquid disposed within said pressure vessel interposed between said pressurization port and said mercury to transmit continuous pressurization from said pressurization port to said mercury.

4. An apparatus for determining the pore volume distribution of two or more samples by intruding a non-wetting conductive liquid into each of the samples under ascending high pressure up to approximately 60,000 psi, comprising:

a cylindrical housing having a strategically sized and shaped internal cavity disposed along a longitudinal axis of said housing, said cavity including means for receiving at least two penetrometers, each penetrometer including a capillary to receive a preselected amount of a conductive non-wetting liquid in intruding relation to each of said penetrometers, said housing including a first housing access aperture;

a housing access cap removably and sealably connectable to said first housing access aperture, said housing access cap having means for receiving at least a portion of each of said capillaries and for providing capacitance plates; and means for electrical connection to each of said penetrometers;

said housing and said housing access cap, together defining a high pressure vessel for ascending pressurization of each penetrometer intruding said non-wetting conductive liquid into said samples, and including means for simultaneous measurement of said ascending pressure and a capacitance change of said conductive non-wetting liquid and said housing access cap capacitance plates.

5. The apparatus of claim 4 wherein said non-wetting liquid is mercury.

6. The apparatus of claim 5 further including a pressurization port in fluid communication with said housing chamber and an incompressible liquid disposed within said housing chamber interposed between said pressurization port and said mercury to transmit continuous pressurization from said pressurization port to said mercury.

7. A method for simultaneously determining the pore volume distribution of two samples by intruding a non-wetting liquid into each of the samples under continuously or step-wise ascending pressure, comprising the steps of:

a) providing a high pressure vessel having a cavity for receiving two or more individual penetrometers through a single access port, each containing a test sample with a preselected quantity of non-wetting liquid in intruding relation to each sample;

b) pressurizing said pressure vessel with continuously or step-wise ascending pressure intruding the non-wetting liquid into each sample;

c) measuring the capacitance of each of a pair of capacitors formed between the pressure vessel and each quantity of non-wetting liquid adjacent each test sample; and d) converting said capacitance value for each pair of capacitors to a pore volume for each test sample.

8. The method of claim 7 wherein step d) includes the following steps:

converting an analog voltage, representing the capacitance for each test sample, to two digital voltages; and inputting said two digital voltages into a computer.

9. The method of claim 8 further including:

converting said two digital voltages to a serial bit stream prior to inputting to said computer.

10. The method of claim 9 further including the step of measuring and inputting to said computer the ascending pressure.

11. A high pressure mercury porosimeter for determining the pore volume distribution of two or more individual samples by intruding and extruding a non-wetting electrically conductive liquid into each of the samples under continuous or step-wise ascending and descending pressures at and above ambient pressure comprising:

a housing having an internal cavity, said cavity strategically sized in volume and configured in shape to receive at least two penetrometers, each penetrometer having a capillary capable of receiving a preselected amount of a non-wetting liquid, said housing including one access sample loading port to said cavity;

a sealable, removable closure for sealing said housing sample loading access port removably connected to said access sample loading port; and means connected inside of said housing for measuring the volume of said non-wetting liquid as a function of internal pressure.

12. A high pressure mercury porosimeter as in claim 11, wherein:

said housing internal chamber can receive a non-compressible fluid and obtain pressures of approximately 60,000 psi; and means for subjecting said non-wetting liquid within said housing internal chamber to pressures of approximately 60,000 psi mounted outside said chamber.

13. A method for simultaneously determining the pore volume distribution of two samples by intruding a non-wetting liquid into each of the samples under continuous or step-wise ascending and descending pressure comprising the steps of:

(a) providing a high pressure vessel capable of sustaining pressure of approximately up to 60,000 psi having a cavity sized and shaped for receiving two or more individual penetrometers through a single access port, each penetrometer containing a test sample with a preselected quantity of non-wetting liquid in intruding relation to each sample;

(b) pressurizing said high pressure vessel with continuously or step-wise ascending and descending pressure for intruding and extruding a non-wetting liquid into each sample independently;

(c) measuring the volumes of the non-wetting liquid inside said high pressure vessel chamber as a function of pressure; and (d) converting said volume of said non-wetting liquid to a pore volume for each test sample.

* * * * *